(12) United States Patent
Goodman et al.

(10) Patent No.: US 6,919,207 B2
(45) Date of Patent: Jul. 19, 2005

(54) METHOD FOR REGULATING GENES WITH ELECTROMAGNETIC RESPONSE ELEMENTS

(75) Inventors: Reba Goodman, Englewood, NJ (US); Hana Lin, Fort Lee, NJ (US); Martin Blank, Tenafly, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/769,902

(22) Filed: Jan. 25, 2001

(65) Prior Publication Data

US 2002/0099026 A1 Jul. 25, 2002

(51) Int. Cl.[7] .................. C12N 15/63; C12N 21/04; A61K 48/00
(52) U.S. Cl. .................. 435/455; 435/320.1; 536/23.1; 536/23.2; 536/24.1; 514/44
(58) Field of Search .................. 435/455, 320.1, 435/23.1, 23.2, 24.1; 536/23.1, 23.2, 24.1; 514/44

(56) References Cited

PUBLICATIONS

Tofani et al. Static and ELF magnetic fields induce tumor growth inhibition and apoptosis. Bioelectromagnetics. Sep. 2001;22(6):419–28.*
DiCarlo et al. A simple experiment to study electromagnetic field effects: protection induced by short–term exposures to 60 Hz magnetic fields. Bioelectromagnetics. 1998;19(8):498–500.*
Kapturczak et al. Curr Mol Med. May 2001;1(2):245–58.*
Collateral Therapeutics, Inc. (Public release) at http://www.eurekalert.org/pub_release/2001–12/ct–nrol12601.php.*
Arnone et al. The hardwiring of development: organization and function of genomic regulatory systems. Development. May 1997;124(10):1851–64.*
Blank et al. Electromagnetic initiation of transcription at specific DNA sites. J Cell Biochem. 2001;81(4):689–92.*
Campbell et al. Adenovirus–mediated p16INK4 gene transfer significantly suppresses human breast cancer growth. Cancer Gene Ther. Sep. 2000;7(9):1270–8.*
Lin et al. A magnetic field–responsive domain in the human HSP70 promoter. J Cell Biochem. Oct. 1, 1999;75(1):170–6.*
Lin et al. Magnetic field activation of protein–DNA binding. J Cell Biochem. Sep. 1, 1998;70(3):297–303.*
Lin et al. Myc–mediated transactivation of HSP70 expression following exposure to magnetic fields. J Cell Biochem. May 1, 1998;69(2):181–8.*
Tomiyasu et al. Direct intra–cardiomuscular transfer of beta2–adrenergic receptor gene augments cardiac output in cardiomyopathic hamsters. Gene Ther. Dec. 2000;7(24):2087–93.*
Zang et al. Adenovirus 5 E1a–mediated gene therapy for human ovarian cancer cells in vitro and in vivo. Int J Gynecol Cancer. Jan.–Feb. 2001;11(1):18–23.*
Rosengart et al. Six–month assessment of a phase I trial of angiogenic gene therapy for the treatment of coronary artery disease using direct intramyocardial administration of an adenovirus vector expressing the VEGF121 cDNA. Ann Surg. Oct. 1999;230(4):466.*
Navarro et al. Efficient gene transfer and long–term expression in neurons using a recombinant adenovirus with a neuron–specific promoter. Gene Ther. Nov. 1999;6(11):1884–92.*
Park et al. Therapeutic levels of human factor VIII and IX using HIV–1–based lentiviral vectors in mouse liver. Blood. Aug. 1, 2000;96(3):1173–6.*
Kon et al. Naked plasmid–mediated gene transfer to skeletal muscle ameliorates diabetes mellitus. J Gene Med. May–Jun. 1999;1(3):186–94.*
Hana Lin et al Specific Region of the c–myc Promoter is Responsive to Electric and Magnetic Fields Journal of Cellular Biochemistry 54:281–288(1994).*
Li Han etal Application of Magnetic Field–Induced Heat Shock Protein 70 for Presurgical Cytoprotection Journal of Cellular Biochemistry 71:577–583(1998).*
Hana Lin etal Regulating Genes with Electromagnetic Response Elements Journal of Celluar Biochemistry 81:143–148 (2001).*
Ming Jin etal Biological and technical variables in myc expression in HL60 cells exposed to 60 Hz electromagnetic fields Bioelectrochem Bioenerg Vo; 44 No 1 pp. 111–120.*
Marshall, E. Gene therapy's growing pains. Science. Aug. 25, 1995;269(5227):1050, 1052–5.*
Junkersdorf et al. Electromagnetic fields enhance the stress response at elevated temperatures in the nematode *Caenorhabditis elegans*. Bioelectromagnetics. Feb. 2000;21(2):100–6.*
Wang et al. Sustained expression of therapeutic level of factor IX in hemophilia B dogs by AAV–mediated gene therapy in liver. Mol Ther. Feb. 2000;1(2):154–8.*

(Continued)

*Primary Examiner*—David Guzo
*Assistant Examiner*—Daniel M. Sullivan
(74) *Attorney, Agent, or Firm*—John P. White, Esq.; Cooper & Dunham LLP

(57) ABSTRACT

A non-invasive method for gene regulation during gene therapy comprises the steps of introducing electromagnetic field response elements into a gene promoter not having any electromagnetic field response elements to serve as switches for regulating exogenously introduced genes, and applying an electromagnetic field to the introduced electromagnetic field response elements to induce gene expression. In this way, a safer, more effective, and more precise method for gene therapy is provided of inducing production of desired genetic products.

5 Claims, No Drawings

PUBLICATIONS

Ross et al. Gene therapy in the United States: a five-year status report. Hum Gene Ther. Sep. 10, 1996;7(14):1781–90.*

Verma et al. Gene therapy—promises, problems and prospects. Nature. Sep. 18, 1997;389(6648):239–42.*

Rux et al. Type–specific epitope locations revealed by X-ray crystallographic study of adenovirus type 5 hexon. Mol Ther. Jan. 2000;1(1):18–30.*

Orkin et al. Report and recommendations of the panel to assess the NIH investment in research on gene therapy. Dec. 7, 1995, available through NIH or at http://www.nih.gov/news/panelrep. html.*

Jindal et al. Prevention of diabetes in the NOD mouse by intra–muscular injection of recombinant adeno–associated virus containing the preproinsulin II gene. Int J Exp Diabetes Res. 2001;2(2):129–38.*

Ye et al. Regulated delivery of therapeutic proteins after in vivo somatic cell gene transfer. Science. Jan. 1, 1999;283(5398):88–91.*

Edelberg et al. Enhancement of murine cardiac chronotropy by the molecular transfer of the human beta2 adrenergic receptor cDNA. J Clin Invest. Jan. 15, 1998;101(2):337–43.*

Edelberg et al. Molecular enhancement of porcine cardiac chronotropy. Heart. Nov. 2001;86(5):559–62.*

Steiner et al. Antisense c–myc retroviral vector suppresses established human prostate cancer. Hum Gene Ther. Mar. 20, 1998;9(5):747–55.*

Huang et al. [Using Hsp70 promoter to regulate target gene expression in tumor] Zhonghua Bing Li Xue Za Zhi. Jun. 2001;30(3):198–201.*

Madio et al. On the feasibility of MRI–guided focused ultrasound for local induction of gene expression. J Magn Reson Imaging. Jan.–Feb. 1998;8(1):101–4.*

Okano et al. Modulatory effects of static magnetic fields on blood pressure in rabbits. Bioelectromagnetics. Sep. 2001;22(6):408–18.*

Blank, M. et al. Electromagnetic fields may act directly on DNA. Journal of Cellular Biochemistry. 1999, vol. 75, pp. 369–374.

Lin et al. Electromagnetic field exposure induces rapid, transitory heat shock factor activation in human cells. Journal of Cellular Biochemistry. 1997, vol. 66, pp. 482–488.

Goodman, R. et al. Magnetic field stress induces expression of hsp70. Cell Stress Chaperones. 1998, vol. 3, No. 2, pp. 79–88.

* cited by examiner

METHOD FOR REGULATING GENES WITH ELECTROMAGNETIC RESPONSE ELEMENTS

BACKGROUND OF THE INVENTION

Throughout this application, various publications are referenced to by arabic numerals within parentheses. Disclosures of these publications in their entireties are hereby incorporated by reference into this application to more fully describe the state of the art to which this invention pertains. Full bibliographic citations for these references may be found at the end of this application, preceding the claims.

Gene therapy was proposed approximately 20 years ago as a way to ameliorate genetic defects by providing a source for missing essential genetic components. The injection of copies of the gene responsible for the production of a specific protein directly into the targeted area by means of a viral vector was considered a mode of insuring that the protein required would be synthesized at the site where it was needed. This approach offered a distinct advantage over prior conventional treatment of metabolic diseases, which required continuous injection of gene product from exogenous sources.

The principle behind gene therapy is simple; however, practical application has been difficult. Failure of early gene therapy was mainly due to three problems. Firstly, there were difficulties in efficiently transducing primary quiescent human cells in vivo. Secondly, there were strong immune responses to the gene therapy vectors, as well as to the foreign therapeutic transgenes that rapidly eliminated transgene expressing cells in humans. Thirdly, there was an ability of many cell types to shut off the viral promoters that controlled transgene expression in humans.

One positive outcome of these early efforts of gene therapy was the demonstration that introducing cloned genes into humans could be safe, with little or no morbidity. More recently, new vectors have been engineered, including adenoviruses and even naked DNA, enhancing the efficiency of in vivo gene delivery and reducing the immunogenicity of vectors and transgenes.

There is a need for a safer, more effective, and more precise method of gene therapy.

SUMMARY OF THE INVENTION

The present invention provides a unique method for gene regulation, using electromagnetic response elements. In the present invention, exogenously introduced genes, in gene therapy, are regulated by the introduction of electromagnetic response elements (EMREs) into the gene promoters that do not have them to serve as "switches." Exposure to electromagnetic fields of 8 $\mu$T 60 Hz for 30 minutes induces gene expression, because the switches make the gene now responsive to EM fields. The electromagnetic field response elements, therefore, are the "switches." The present invention therefore provides a non-invasive technique in gene therapy.

In this way, a safer, more effective, and more precise method for gene therapy is provided for inducing production of desired gene products. The present invention is therefore an improvement over the invasive character of current gene therapy protocols.

The electromagnetic field response elements, therefore, can be introduced into any gene promoter not having them. Examples are insulin and the cystic fibrosis gene. The electromagnetic field response elements can be introduced into any gene that would supply a missing gene product that the person does not already have due to some genetic consequence.

The present invention not only regulates and programs gene promoters to induce genetic information, but it does so in a patient-friendly manner.

Applying an electromagnetic field to the introduced gene containing the new electromagnetic field response elements induces gene expression.

In summary, the present invention in one embodiment provides a non-invasive method for gene regulation during gene therapy, comprising the steps of: introducing electromagnetic field response elements into a gene promoter not having any electromagnetic field response elements to serve as switches for regulating exogenously introduced genes; and applying an electromagnetic field to the introduced electromagnetic field response elements to induce gene expression.

The present invention in another embodiment provides a non-invasive method for gene regulation during gene therapy, comprising the steps of: introducing at least one electromagnetic field response element into a gene promoter not having any electromagnetic field response elements to serve as switches for regulating exogenously introduced genes; and applying an electromagnetic field to each introduced electromagnetic field response element to induce gene expression.

DETAILED DESCRIPTION OF THE INVENTION

The present invention in one embodiment provides a non-invasive method for gene regulation during gene therapy, comprising the steps of: introducing electromagnetic field response elements into a gene promoter not having any electromagnetic field response elements to serve as switches for regulating exogenously introduced genes; and applying an electromagnetic field to the introduced electromagnetic field response elements to induce gene expression.

The introduced electromagnetic field response elements may be nCTCTn sequences in an HSP70 gene promoter. A number of the nCTCTn sequences may be 3. The nCTCTn sequences may lie between about −230 and about −160 in the HSP70 gene promoter.

The introduced electromagnetic field response elements may be nCTCTn sequences in a c-myc gene promoter. A number of the nCTCTn sequences may be 8. The nCTCTn sequences may lie between about −1257 and about −353 in the c-myc gene promoter.

The electromagnetic field is preferably applied at a field strength of about 8 $\mu$T and a frequency of about 60 Hz for a time of about 30 minutes.

The present invention in another embodiment provides a non-invasive method for gene regulation during gene therapy, comprising the steps of: introducing at least one electromagnetic field response element into a gene promoter not having any electromagnetic field response elements to serve as switches for regulating exogenously introduced genes; and applying an electromagnetic field to each introduced electromagnetic field response element to induce gene expression.

Each introduced electromagnetic field response element may be an nCTCTn sequence in an HSP70 gene promoter. Each introduced electromagnetic field response element may be an nCTCTn sequence in a c-myc gene promoter. The electromagnetic field is preferably applied at a field strength of about 8 $\mu$T and a frequency of about 60 Hz for a time of about 30 minutes.

Low frequency electromagnetic (EM) fields induce increased expression of the stress response gene HSP70 (6) (2). There are several parallels in the biochemical pathways induced by electromagnetic fields and heat shock, but there are striking differences as well. Both pathways involve the binding of heat shock factor 1 (HSF1) to a heat shock element (HSE), but regulation of HSP70 gene expression by electromagnetic fields involves three nCTCTn binding sites in the HSP70 promoter that lie between −230 and −160, upstream from the transcription initiation site. These three nCTCTn sequences appear to act as electromagnetic field response elements (EMREs), since the ability of an electromagnetic field to induce stress proteins gradually disappears as the EMREs are mutated one by one (7) (9). Removal of EMREs by mutation does not affect the response to heat shock, since the heat shock domain is downstream from the electromagnetic field domain in the HSP70 promoter, i.e., between −106 and −67 (6) (8) (9).

A 900 bp region in the c-myc promoter (−1257 to −353) is responsive to electromagnetic fields (5). Recent reanalysis of this 900 bp region revealed eight nCTCTn sequences within this DNA fragment. These eight EMREs in the c-myc promoter could account for the electromagnetic field sensitivity of the c-myc gene, and the resultant increased c-myc transcript levels in cells exposed to electromagnetic fields (4).

To determine whether EMREs can serve as switches to regulate exogenously introduced genes, the 900 bp fragment of the c-myc promoter was placed upstream of CAT (chloramphenicol transferase) or luciferase reporter constructs that were otherwise unresponsive to electromagnetic fields. EMRE-reporter constructs were transfected into HeLa cells and transfectants exposed to electromagnetic fields. Protein extracted from EM field-exposed transfectants showed increased CAT and luciferase activities, whereas no increase in CAT or luciferase was measurable in the unexposed controls. Three kinds of controls were used: transfectants that were sham-exposed, transfectants lacking EMREs, and non-specific protein. These data support the theory that EMREs can be inserted into the promoters of exogenously introduced genes to serve as switches that respond to electromagnetic fields. This would provide a new and powerful non-invasive technique for regulating gene expression during gene therapy.

Materials and Methods

Cell Culture and Transfections

As previously described, HeLa cells were used for transient transfections and the lipofectin method (Gibco/BRL, Cat # 18292-011) was used for transfection as described (6) (7) (8).

900 bp Segment from the c-myc Promoter

The 900 bp region of the c-myc promoter containing eight copies of nCTCTn extends from −353 (PVUII site) to −1257 (ClaI site)

pΔH-11-CAT HSP70 Deletion Construct

A diagrammatic representation of this construct is presented in reference (9). This construct contains the first 111 base pairs upstream from the transcription initiation site and includes the heat shock domain (−106 to −67). There are no nCTCTn binding sites in this construct and it is not responsive to electromagnetic fields (9).

Protein

Protein was extracted and concentrations determined as previously described (6) (7) (8) (9).

CAT Assay

CAT assays were performed as previously described (6) (7). Results were quantified using a PhosphorImager and ImageQuant software.

Luciferase Assay

Luciferase activity was determined (Luciferase Assay Kit) (Promega #E1501) and results quantified as suggested by Promega.

Magnetic Field Exposures of Transfectants

Transfectants were exposed and sham-exposed as previously described (7) (9).

Heat Shock

Samples from cells that had been heat shocked (43° C.) served as positive controls for CAT assay. Petri dishes containing transfectants were wrapped in Parafilm, placed in a mu metal box (to shield them from exposure to the magnetic fields generated by the water bath heating motor) and immersed in the water bath at 43° C. for 30 minutes. Petri dishes were removed from the water bath and, following an additional 30 minutes at 37° C., protein was extracted (3) (6).

Electromagnetic Field Exposure System

Two fully functional exposure units provided simultaneous sham and experimental exposures. Exposures used Helmholtz coils (Electric Research and Management, Pittsburgh, Pa.) that consisted of 19-gauge wire bundles wound 164 times around a square form 13 cm long and 14 cm wide with 8 cm spacing. The coils were energized by a function generator (11 MHz Wavetek Stabilized Function Generator, model 21). A digital multimeter was used to measure the field intensity and verify the systems operation (Fluke 87 digital multimeter). Field parameters were monitored with a Hitachi V-1065 100 MHz oscilloscope and calibrated inductive search coil (25×; Electro-Biology Inc., Parsippany, N.J.). Detailed description of the exposure system, including background magnetic fields in the incubator, harmonic distortion, DC magnetic fields and mean static magnetic fields in the incubator, both vertical and horizontal components, can be found in reference (4). Cells were placed on a Plexiglas stand in a horizontal orientation; i.e., the entire area of the dish was exposed to the field. The bottom of the dish was 2 cm below the axis level. The height from dish bottom to top surface of liquid was approximately 1.1 cm. The height of the liquid was 0.6 cm. The calculated electric field was ~11 $\mu$V/m for an 8 $\mu$T exposure.

Mu Metal Shielding

Helmholtz coils were enclosed within Mu metal containers to minimize stray fields during electromagnetic field exposures. Both active (experimental) and sham-exposed coils (controls) were enclosed in a 30 cm high, 15 cm diameter cylindrical mu metal container (0.040" thickness) (Amuneal Corp. Philadelphia, Pa.). The 60 Hz shielding factor is (Min.) 90.1 (39.08 dB) Sham-exposed controls and experimental exposures are performed simultaneously in identical mu metal containers.

Statistical Analyses

A sufficient number of experiments were performed to assure statistical significance. Statistical significance is determined by a multifactor analysis of variance program (INSTAT).

Discussion

Because electromagnetic fields penetrate tissues without attenuation, they must penetrate to the cell nucleus with its DNA and interact with moving charges there (1). There are conducting electrons in DNA (12), and direct measurements of electrical transport through DNA have been made. The dynamics of DNA-mediated electron transfer at the femtosecond level have been measured (14). Conduction in DNA appears to depend on specific structure, since different DNA sequences have different conductivities (10). Therefore, electromagnetic fields could theoretically interact preferentially with specific DNA sequences, and the nCTCTn sequences (EMREs) in the HSP70 and c-myc promoters used in these studies may be such sequences.

We have shown that these sequences are critical for electromagnetic field responsiveness in our experiments, and other data appear to support this. In totally unrelated investigations, one study showed that low frequency electromagnetic field stimulation in nigro-striatal lesioned rats with chromaffin transplants induced changes in the subventricular zones and led to significant motor improvements in a rat Parkinson model (13). A second report from the same laboratory has used differential display to analyze possible alterations in DNA of electromagnetic field-exposed chromaffin cells.

Differential bands observed in the EM field-exposed group show changes in gene expression induced by electromagnetic fields. One specific differential band in the EM field-exposed samples, containing 349 bp, was sequenced. In an independent analysis of this DNA fragment, we have identified three copies of the electromagnetic field response element (nCTCTn) that we described herein. A computer search may determine whether this 349 bp DNA fragment is contained in the promoters of any known genes, possibly a specific gene related to the differentiation process of chromaffin cells.

Electromagnetic fields induce gene expression (2) (9) and activation of the gene by electromagnetic fields requires specific EMREs, which control genes when placed upstream of reporter constructs. Their ability to confer electromagnetic field responsiveness suggests the use of EMREs in the control and regulation of gene therapy. The characterization of a cellular promoter system that can be regulated, such as described here, provides a novel, noninvasive, technique for the regulation of transgene expression in humans without interfering with normal physiologic function. The applied electromagnetic field can be directed to the region where the gene product is needed, and, since the electromagnetic field intensities needed to affect EMREs are well below the human perception threshold, their introduction and presence would not be felt by the patient.

An example of such application would be the introduction of an exogenous insulin gene containing one or more EMREs placed upstream of the gene. Regulation would be provided by the simple and safe application of electromagnetic fields. The whole operation would be made automatic by having the EM field generating circuit activated by an implanted glucose sensor responsive to pre-set blood glucose levels.

Our results show that the eight nCTCTn sequences (EMREs) in the 900 bp DNA fragment from the c-myc promoter are effective in regulating CAT or luciferase activity. However, not all eight EMREs may be needed for a response (9). The EM-induced expression of HSP70 is mediated through three EMREs in the human HSP70 promoter. Electromagnetic field exposure of HSP70 promoter constructs, linked to a CAT reporter gene and containing all three sites, showed more than a three fold increase in CAT activity. Yet, the presence of even one site was sufficient for a 1.5 fold increased CAT response. These data show that even a single EMRE can promote interaction with electromagnetic fields. The data also suggest that the level of interaction appears to be roughly proportional to the number of EMREs.

According to an embodiment of this invention, then, nCTCTn sequences, taken from the myc promoter, were attached to HSP70 constructs that didn't contain them. The HSP70 promoter has three nCTCTn sequences in the electromagnetic field domain (230-160), but none in the heat shock domain (111-67). When the nCTCTn sequences are inserted into the heat shock domain (which was previously responsive only to heat and not to electromagnetic fields) this promoter construct that previously did not respond to EM fields, now does respond and induces gene expression.

In this way, electromagnetic field response elements, i.e., nCTCTn sequences from the c-myc promoter, are actively incorporated into the HSP70 promoter and regulate and program gene expression; thus, inserting these nCTCTn sequences into a reporter construct (CAT or Luciferase) that was previously unresponsive to EM fields, renders the gene electromagnetic field-responsive, and induces the gene activity.

Summary

A 900 base pair segment of the c-myc promoter, containing eight nCTCTn sequences, induces c-myc expression by electromagnetic fields. Similarly, a 70 bp region of the HSP70 promoter, containing three nCTCTn sequences, induces HSP70 expression by electromagnetic fields. Removal of the 900 base pair segment of the c-myc promoter eliminates the ability of electromagnetic fields to induce c-myc expression. Similarly, removal of the 70 bp region of the HSP70 promoter, with its three nCTCTn sequences, eliminates the response to electromagnetic fields. The nCTCTn sequences apparently act as electromagnetic field response elements (EMREs). To test whether introducing EMREs imparts the ability to respond to applied electromagnetic fields, the 900 bp segment of the c-myc promoter (containing eight EMREs) was placed upstream of CAT or luciferase reporter constructs that were otherwise unresponsive to electromagnetic fields. EMREs-reporter constructs were transfected into HeLa cells and exposed to 8 $\mu$T 60 Hz fields. Protein extracts from EM field-exposed transfectants had significant increases in activity of both CAT and luciferase, compared with identical transfectants that were sham-exposed. Transfectants with CAT or luciferase constructs lacking EMREs remained unresponsive to EM fields; that is, there was no increase in either CAT or luciferase activity. These data support the idea that EMREs can be used as switches to regulate exogenously introduced genes in gene therapy.

Although embodiments of the invention have been described herein, numerous variations and modifications will occur to those skilled in the art without departing from the scope of the invention. The invention is not limited to the embodiments disclosed, and is defined only by way of the following claims.

REFERENCES

1. M. Blank and R. Goodman. Electromagnetic Fields May Act Directly on DNA. J Cell Biochem 75:369–374 (1999).
2. R. Goodman and M. Blank. Magnetic Field Stress Induces Expression of hsp70. Cell Stress & Chaperones 3:79–88 (1998).

3. Mosser et al. Molecular Cell Biology. 8: 4736–4744 (1988).
4. M. Jin, H. Lin, L. Han, M. Opler, S. Maurer, M. Blank, R. Goodman. Biological and Technical Variables In myc Expression in HL60 Cells Exposed to 60 Hz Electromagnetic Fields. Bioelectrochem Bioenerg 44:210–217 (1997).
5. H. Lin, R. Goodman, A. S. Henderson. Specific Region of the c-myc Promoter is Responsive to Electric and Magnetic Fields. J Cell Biochem 54:281–288 (1994).
6. H. Lin, M. Opler, M. Head, M. Blank, R. Goodman. Electromagnetic Field Exposure Induces Rapid, Transitory Heat Shock Factor Activation In Human Cells. J Cell Biochem 66:482–488 (1997).
7. H. Lin, M. Head, M. Blank, L. Han, M. Jin, R. Goodman. Myc-Mediated Transactivation of HSP70 Expression Following Exposure to Magnetic Fields. J Cell Biochem 69:181–188 (1998a).
8. H. Lin, M. Head, M. Blank, L. Han, R. Goodman. Magnetic Field Activation of Protein-DNA Binding. J Cell Biochem 70 297–303 (1998b).
9. H. Lin, M. Blank, R. Goodman. Magnetic Field-Responsive Domain in the Human HSP70 Promoter. J Cell Biochem 75:170–176 (1999).
10. E. Meggers, M. E. Michel-Beyerle, B. Giese. Sequence Dependent Long Range Hole Transport in DNA. J Am Chem Soc 120:12950–12955 (1998).
11. T. Olivares-Banuelos, L. Verdugo-Diaz, L. Navarro, M. A. Q. Merez, R. Drucker-Colin. Changes in Gene Expression Induced by Elf mf in Differentiated Chromaffin Cells. Bioelectrochem.Bioenerg. in press (2000).
12. D. Porath, A. Berzyadin, S. de Vries, C. Dekker. Direct Measurement of Electrical Transport Through DNA Molecules. Nature 403: 635–638 (2000).
13. L. Verdugo-Diaz, A. Feria-Velasco, S. Orozco-Suarez, R. Drucker-Colin. Low Frequency Magnetic Field Stimulation in Nigro-Striatal Lesioned Rats With Chromaffin Cell Transplants Induces Changes in the Subventricular Zone. Proc Natl Acad Sci (USA) in press (2000).
14. C. Wan, T. Fiebig, S. O. Kelley, C. R. Treadway, J. K. Barton. Femtosecond Dynamics of DNA-Mediated Electron Transfer. Proc Nat Acad Sci USA 96 6014–6019 (1999).

We claim:

1. An in vitro method for regulating the expression of an exogenous gene introduced into a cell comprising the steps of:

(a) providing a gene promoter comprising a 900 base pair segment of a c-myc promoter containing nCTCTn electromagnetic field response elements fused to a HSP70 gene promoter heat shock responsive element;

(b) introducing the gene promoter from step (a) into the exogenous gene so that the promoter controls the expression of the exogenous gene;

(c) applying an electromagnetic field to the nCTCTn erectromagnetic field response elements so as to thereby regulate expression of the exogenous gene introduced into the cell.

2. The method as set forth in claim 1, wherein the electromagnetic field is applied at a field strength of about 8 $\mu$T and a frequency of about 60 Hz for a time of about 30 minutes.

3. An expression vector comprising a gene promoter comprising a 900 base pair segment of c-myc promoter containing nCTCTn electromagnetic field response elements fused to a HSP70 gene promoter heat shock responsive element.

4. An in vitro method for regulating the expression of a nucleic acid in a cell comprising applying an electromagnetic field to a cell having therein an expression vector comprising a gene promoter comprising a 900 base pair segment of a c-myc promoter containing nCTCTn electromagnetic field response elements fused to a HSP70 gene promoter heat shock responsive element wherein the gene promoter permits the expression of the nucleic acid, so as to thereby regulate the expression of the nucleic acid in the cell.

5. The method in claim 4 wherein the electromagnetic field is applied at a field strength of about 8 $\mu$T and a frequency of about 60 Hz for a time of about 30 minutes.

* * * * *

SEQUENCE LISTING

```
<160> NUMBER OF SEQ ID NOS: 2

<210> SEQ ID NO 1
<211> LENGTH: 29
<212> TYPE: DNA
<213> ORGANISM: artificial sequence
<220> FEATURE:
<223> OTHER INFORMATION: primer incorporating restriction site

<400> SEQUENCE: 1
cctgagctct tctttgatca gaatcgata                                    29

<210> SEQ ID NO 2
<211> LENGTH: 27
<212> TYPE: DNA
<213> ORGANISM: artificial sequence
<220> FEATURE:
<223> OTHER INFORMATION: primer incorporating restriction site

<400> SEQUENCE: 2
tctaagcttc tttgatcaga atcgatg                                      27
```